(12) United States Patent
Horiike

(10) Patent No.: US 10,854,168 B2
(45) Date of Patent: Dec. 1, 2020

(54) INFORMATION PROCESSING APPARATUS, INFORMATION PROCESSING METHOD, AND INFORMATION PROCESSING SYSTEM

(71) Applicant: SONY CORPORATION, Tokyo (JP)

(72) Inventor: Koichi Horiike, Tokyo (JP)

(73) Assignee: SONY CORPORATION, Tokyo (JP)

( * ) Notice: Subject to any disclaimer, the term of this patent is extended or adjusted under 35 U.S.C. 154(b) by 79 days.

(21) Appl. No.: 15/553,192

(22) PCT Filed: Feb. 3, 2016

(86) PCT No.: PCT/JP2016/053136
§ 371 (c)(1),
(2) Date: Aug. 24, 2017

(87) PCT Pub. No.: WO2016/158000
PCT Pub. Date: Oct. 6, 2016

(65) Prior Publication Data
US 2018/0122333 A1    May 3, 2018

(30) Foreign Application Priority Data

Mar. 30, 2015  (JP) ................................ 2015-068899

(51) Int. Cl.
*G06F 3/048* (2013.01)
*G09G 5/08* (2006.01)
(Continued)

(52) U.S. Cl.
CPC ........... *G09G 5/08* (2013.01); *A61B 1/00048* (2013.01); *A61B 90/00* (2016.02); *A61B 90/37* (2016.02); *G06F 3/01* (2013.01); *G06F 3/013* (2013.01); *G06F 3/017* (2013.01); *G06F 3/0481* (2013.01); *G06F 3/1454* (2013.01); *G09G 5/00* (2013.01); *G16H 20/40* (2018.01); *G16H 80/00* (2018.01); *H04L 65/4015* (2013.01); *H04N 5/64* (2013.01); *H04N 7/18* (2013.01);
(Continued)

(58) Field of Classification Search
None
See application file for complete search history.

(56) References Cited

U.S. PATENT DOCUMENTS

| 9,538,962 B1* | 1/2017 | Hannaford | A61B 5/7445 |
| 2006/0082542 A1* | 4/2006 | Morita | A61B 5/7475 |
| | | | 345/156 |

(Continued)

FOREIGN PATENT DOCUMENTS

| JP | 8-171586 A | 7/1996 |
| JP | 2001-117046 A | 4/2001 |

(Continued)

*Primary Examiner* — William C Trapanese
(74) *Attorney, Agent, or Firm* — Xensus LLP

(57) ABSTRACT

[Object] To provide an information processing apparatus which can make mutual communication smooth when a surgery is carried out while sharing an image between a plurality of users.
[Solution] Provided is an information processing apparatus including: a processing unit configured to change a pointer attribute of a pointer displayed in accordance with a position designated by a user on a display region of a head mounted display, on the basis of a user attribute of the user who wears the head mounted display.

18 Claims, 8 Drawing Sheets

(51) Int. Cl.

| | |
|---|---|
| *G09G 5/00* | (2006.01) |
| *H04N 7/18* | (2006.01) |
| *G06F 3/0481* | (2013.01) |
| *A61B 90/00* | (2016.01) |
| *G06F 3/01* | (2006.01) |
| *H04N 5/64* | (2006.01) |
| *H04L 29/06* | (2006.01) |
| *G16H 20/40* | (2018.01) |
| *G16H 80/00* | (2018.01) |
| *A61B 1/00* | (2006.01) |
| *G06F 3/14* | (2006.01) |
| *G02B 27/01* | (2006.01) |
| *A61B 90/50* | (2016.01) |

(52) U.S. Cl.
CPC ...... *A61B 2090/502* (2016.02); *G02B 27/017* (2013.01); *G09G 2340/14* (2013.01); *G09G 2354/00* (2013.01)

(56) References Cited

U.S. PATENT DOCUMENTS

| | | | |
|---|---|---|---|
| 2010/0192107 A1 | 7/2010 | Takahashi | |
| 2010/0231685 A1 | 9/2010 | Kato | |
| 2013/0135180 A1* | 5/2013 | McCulloch | G06F 3/012 345/8 |
| 2014/0176533 A1* | 6/2014 | Dillavou | G06T 19/006 345/419 |
| 2014/0292653 A1 | 10/2014 | Kamba et al. | |
| 2015/0156196 A1* | 6/2015 | Kim | G06F 21/84 345/156 |
| 2016/0018888 A1* | 1/2016 | Buford | G06F 3/013 345/156 |
| 2016/0027218 A1* | 1/2016 | Salter | G02B 27/0172 345/633 |

FOREIGN PATENT DOCUMENTS

| | | |
|---|---|---|
| JP | 2002-368762 A | 12/2002 |
| JP | 2010-170354 A | 8/2010 |
| JP | 2010-213129 A | 9/2010 |
| JP | 2013-54661 A | 3/2013 |

\* cited by examiner

INFORMATION PROCESSING APPARATUS, INFORMATION PROCESSING METHOD, AND INFORMATION PROCESSING SYSTEM

TECHNICAL FIELD

The present invention relates to an information processing apparatus, an information processing method, and an information processing system.

BACKGROUND ART

As one of wearable terminals that a user wears and uses, there is a head mounted display (hereinafter, referred to as "HMD"). The HMD is a display device that is mounted on the head of a user when used and in recent years, the HMD is not only used as AV equipment and a display device for a computer game and the like, but also used as a display device for a user to check information while working in working environment.

On a medical site, for example, the HMD is used as a display device for displaying an image of an endoscope. A surgeon wears the HMD and performs a surgery while viewing an image displayed on the HMD. In the past, an image of the endoscope was usually displayed on a monitor installed in the vicinity of the surgeon, and therefore, it was necessary for the surgeon to frequently move his/her visual line between the monitor and a patient. By displaying the image of the endoscope on the HMD, it is made possible for a surgeon to check the image of the endoscope displayed on the display unit of the HMD and a patient without moving his/her visual line considerably.

Here, in the case where a plurality of users use HMD's, respectively, in a surgery room, it is desirable that the users be able to communicate with each other smoothly. For example, in the case where the plurality of users each wearing the HMD share an identical image (hereinafter, also referred to as "shared image"), with display of a pointer that indicates a specified part within the shared image, instructions can be given appropriately to another user (for example, Patent Literature 1).

CITATION LIST

Patent Literature

Patent Literature 1: JP 2001-117046A

DISCLOSURE OF INVENTION

Technical Problem

However, if all pointers of a plurality of users who watch a shared image are displayed on a display region of the HMD of each user, it is difficult to grasp which pointer belongs to which user, and it becomes difficult for the user to communicate with each other. On the other hand, if the pointers displayed on the display region are easily operable by each user, it is difficult to distinguish the pointer to be operated, and there is a possibility that the pointer that should not be operated is operated.

Accordingly, the present disclosure suggests an information processing apparatus, an information processing method, and an information processing system, which are novel and improved, and which can make mutual communication smooth when a surgery is carried out while sharing an image between a plurality of users.

Solution to Problem

According to the present disclosure, there is provided an information processing apparatus including: a processing unit configured to change a pointer attribute of a pointer displayed in accordance with a position designated by a user on a display region of a head mounted display, on the basis of a user attribute of the user who wears the head mounted display.

Further, according to the present disclosure, there is provided an information processing method including: acquiring a user attribute of a user who wears a head mounted display; and changing a pointer attribute of a pointer displayed in accordance with a position designated by the user on a display region of the head mounted display, on the basis of the user attribute.

Further, according to the present disclosure, there is provided an information processing system including: a head mounted display; and a processing unit configured to change a pointer attribute of a pointer displayed in accordance with a position designated by a user on a display region of the head mounted display, on the basis of a user attribute of the user who wears the head mounted display.

Advantageous Effects of Invention

As described above, according to the present invention, the mutual communication can be made smooth when a surgery is carried out while sharing an image between a plurality of users. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
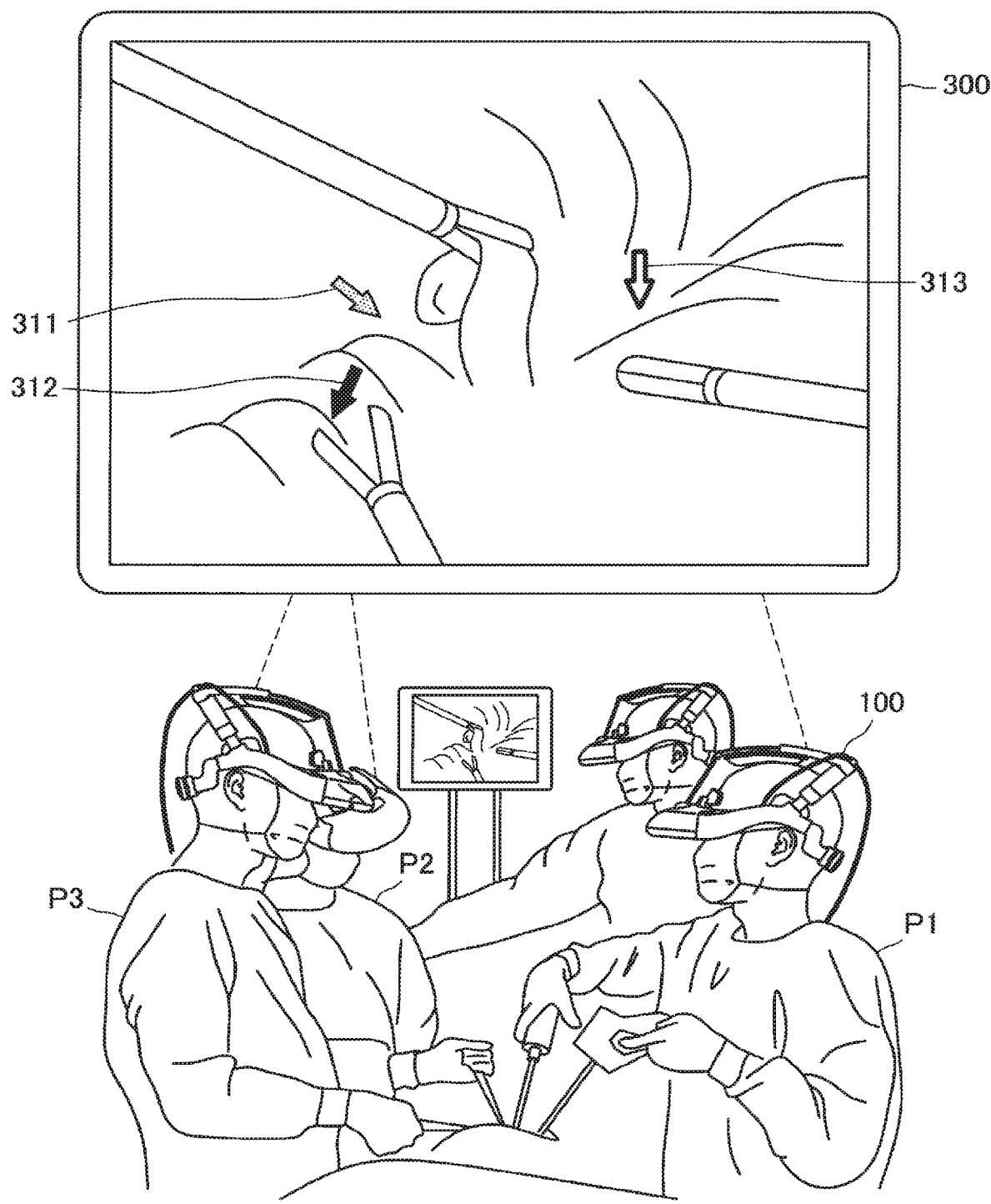
FIG. 1 is an explanatory diagram showing a situation in which an endoscopic surgery is carried out by a plurality of users each wearing an HMD.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that the description will be given in the following order.
1. Overview
2. Configuration
   2.1. HMD
   2.2. Processor unit
3. Display control processing
   3.1. Pointer display processing
   3.2. Pointer operation processing <1. Overview>

First, with reference to FIG. 1, an overview of processing performed by an information processing apparatus according to an embodiment of the present disclosure will be described. Note that FIG. 1 is an explanatory diagram showing a situation in which an endoscopic surgery is carried out by a plurality of users each wearing an HMD 100.

In an endoscopic surgery carried out by a surgeon wearing the HMD 100, as shown in FIG. 1, for example, an image 300 showing a situation of an affected area captured by an endoscope device is displayed on a display unit of the HMD 100, and surgeons carry out the surgery while visually recognizing the displayed image 300. The surgeons are represented by users P1 to P3 of the HMD 100, respectively, and when the users P1 to P3 perform observation by sharing the image 300, as shown in FIG. 1, the display of pointers 311, 312, and 313, which are operable by the respective users, can indicate the respective specified parts in the image 300. In the present embodiment, the pointers 311, 312, and 313 are each operated through a non-contact operation technique such as a gesture or a visual line of the corresponding user. Since the HMD 100 is operable in a non-contact manner and the operation does not disturb the work on the medical site, the operation input by a visual line or a gesture is effective.

Here, in the case where a plurality of pointers are displayed in the image, if the pointers are all displayed in the same manner, it is difficult to know which pointer is the one that is operable by each user and to perform smooth work. Consequently, the information processing apparatus according to the present embodiment changes pointer attributes of the corresponding pointers 311, 312, and 313 in accordance with user attributes of the users P1 to P3. Here, a user attribute is user identification information for identifying a user who uses the HMD, and includes information such as an ID, a belonging, a type of occupation, or a class of the user. Further, the pointer attribute is information showing specifications related to pointer display, such as a shape and a color.

For example, as shown in FIG. 1, colors of the pointers 311, 312, and 313 displayed in the image 300 are made to be different from each other in accordance with the user attributes. In this manner, each of the users P1 to P3 can clearly recognize which pointer is the one that is operable by himself/herself, and can also clearly recognize the other pointers are operated by which users. In this case, additional information may be displayed, which can specify the operator of the pointer such as a user's name, near the displayed pointer.

Further, the information processing apparatus according to the present embodiment may make a pointer of another user operable in accordance with authority information included in a user attribute. The authority information is information showing whether a pointer of another user is operable. For example, a user can operate a pointer of another user whose authority is lower than the authority of the user himself/herself. In this manner, the user having a high authority can operate the pointer of the user having a low authority and can give instructions of work directly to the user having the low authority. Hereinafter, a configuration of the HMD 100 according to the present embodiment and processing performed by the HMD 100 will be described in detail.

<2. Configuration>

Figure 2:
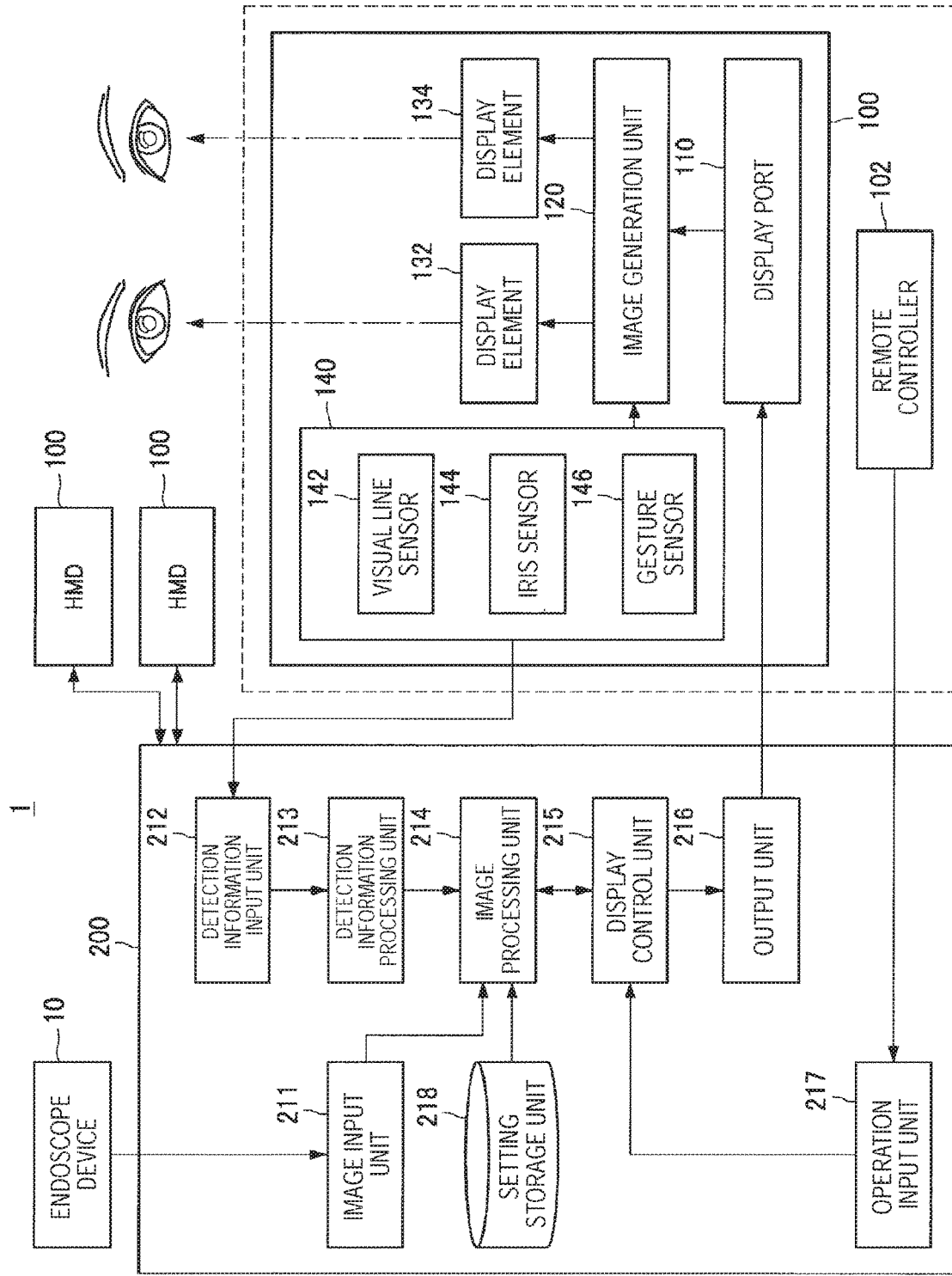
FIG. 2 is a functional block diagram showing functional configurations of an HMD and a processor unit included in an information processing system according to an embodiment of the present disclosure.

First, with reference to FIG. 2, configurations of the HMD 100 and a processor unit 200 included in an information processing system 1 will be described. Note that FIG. 2 is a functional block diagram showing functional configurations of the HMD 100 and the processor unit 200 included in the information processing system 1 according to the present embodiment. Note that FIG. 2 shows functional units which function while display control of a display unit of the HMD 100 is performed, and in practice, other functional units are included. The processor unit 200 functions as a display control device configured to perform display control on the HMD 100, on the basis of operation input to the HMD 100.

[2.1. HMD]

The HMD 100 is a display device that displays information, such as an input image from an external device such as an endoscope device. The HMD 100 is, for example, a non-transmissive HMD in the shape of goggles and is used in a state of being mounted on the head of a user. The HMD 100 includes a main body unit including display units for presenting information to a wearer of the HMD 100, and an upper fixing unit and a rear fixing unit for fixing the main body unit to the head. When the HMD 100 is fixed to the head of the wearer by the fixing units, the display units of the main body unit are located in front of the left and right eyes of the wearer.

The main body unit is a portion that covers both the eyes of the wearer. The main body unit may be configured so as to cover, for example, the parts in the vicinity of the left and right temples of the wearer. By forming the main body unit into such a shape, it is possible to cover the parts in front of the eyes of the wearer almost perfectly when the wearer wears the HMD 100, and therefore, it is made possible for the wearer to easily view an image because no external light enters the wearer's eyes. A camera configured to shoot, for example, peripheral environment, may be provided on a side of the main body unit. Due to this, the wearer wearing the HMD 100 can also recognize information on peripheral environment that is seen when the HMD 100 is not mounted (video see-through), in addition to information provided from the endoscope device and the like via the processor unit 200.

Inside the main body 110, a first display element (reference numeral 132 in FIG. 2) that presents an image for the left eye on a first display unit and a second display element (reference numeral 134 in FIG. 2) that presents an image for the right eye on a second display unit are provided. Each display element presents, for example, an image of the endoscope device provided by the processor unit 200, an image captured by the camera of the main body unit, and the like. Further, the main body unit is also provided with a cable (not shown) that is connected to the processor unit 200 in order to perform transmission and reception of information with the processor unit 200. The information communication between the HMD 100 and the processor unit 200 may be performed via wire or radio.

Information displayed on the display units of the HMD 100 is operable by using a remote controller 102 such as a foot switch which performs input operation by being pushed by a foot of a wearer, or using a visual line or a gesture of the wearer of the HMD 100, for example. The input information from the remote controller 102 and the input information including the visual line direction of the wearer acquired by a visual line detection function or the gesture of the wearer acquired by a gesture detection function are output to the processor unit 200.

Referring to the display processing functions of the HMD 100, as shown in FIG. 2, the HMD 100 includes a display port 110, an image generation unit 120, display elements 132 and 134, and a sensor unit 140.

The display port 110 is an interface that receives input information from the processor unit 200. To the display port 110, a cable that enables information communication with the communication unit 200 is connected. Input to the display port 110 are, for example, image signals to be output to the display elements 132 and 134, respectively, and information visually recognized by a wearer of the HMD 100. The information input from the display port 110 is output to the image generation unit 120.

The image generation unit 120 generates image signals that are output to the display elements 132 and 134, respectively, based on the information acquired via the processor unit 200. In the case where the image presented to a wearer is a 3D image, the image generation unit 120 performs shift processing to produce a shift between a left-eye image signal that is output to the first display element 132 and a right-eye image signal that is output to the second display element 134. In the shift processing, for example, the amount of shift between the left-eye image signal and the right-eye image signal is determined in accordance with, for example, the distance between the display elements 132 and 134 and the wearer's eyes, the interval between wearer's eyes, the virtual image position, and the like. The image generation unit 120 outputs the generated image signal to the first display element 132 and the second display element 134.

Further, the image generation unit 120 generates a pointer image signal on the basis of a result detected by a visual line sensor 142 or a gesture sensor 146 to be described later. The pointer image signal is a signal for displaying a pointer indicating a position designated by a user on a display region. In the case where pieces of information on pointer images of a plurality of users observing a shared image are input, the image generation unit 120 also generates pointer image signals of the other users. The image generation unit 120 superimposes the pointer image signals on the image signal generated on the basis of the information from the processor unit 200, and outputs the resultant to the display elements 132 and 134.

The display elements 132 and 134 emit image light toward the display units on the basis of the image signal input from the image generation unit 120. The display elements 132 and 134 are arranged, for example, so as to face the display units in the longitudinal direction of the wearer's face when the HMD 100 is mounted. Due to this, the optical axis of the image light emitted from the display elements 132 and 134 will become substantially parallel to the direction of the visual line when the wearer faces the front.

The display elements 132 and 134 include, for example, an organic electroluminescence (EL) element. By adopting the organic EL element as the display elements 132 and 134, it is possible to realize compactness, high contrast, quick responsiveness, and the like. The display elements 132 and 134 have a configuration in which, for example, a plurality of red organic EL elements, a plurality of green organic EL elements, a plurality of blue organic EL elements, and the like, are arranged in the form of a matrix. Each of these elements spontaneously emits light at predetermined timing, luminance, and the like, by being driven by a drive circuit of active matrix type, passive matrix type, or the like. By controlling the drive circuit on the basis of the image signal generated in the image generation unit 120, a predetermined image is displayed on the entire display elements 132 and 134 and the image is presented to a wearer via the display units.

Between the display elements 132 and 134 and the display units, as an optical system, for example, a plurality of eyepiece lenses (not shown) may be arranged, respectively. By causing these eyepiece lenses and the wearer's eyes to face each other with a predetermined distance in between, it is made possible to cause a wearer to observe a virtual image, which looks as if an image is displayed at a predetermined position (virtual image position). By presenting such a virtual image, it is possible to provide a 3D image. Note that the virtual image position and size of the virtual image are set by the configuration and the like of the display elements 132 and 134 and the optical system.

The sensor unit 140 includes various sensors that acquire various types of information in the HMD 100. Examples of sensors included in the HMD 100 include a visual line sensor 142, an iris sensor 144, and a gesture sensor 146.

The visual line sensor 142 detects a visual line direction of a user who wears the HMD 100. The visual line sensor 142 is provided at the side opposite to the parts in front of the eyes of the wearer in the main body unit of the HMD 100. The visual line sensor 142 includes, for example, a light source that irradiates the eyeball of the wearer with light in the infrared band (infrared light), and an image capturing unit that captures an image of the eyeball of the wearer. The visual line sensor 142 irradiates the eyeball of the wearer who observes a display plane of the display unit with the light from the light source, and the image capturing unit captures an image of the eyeball which is irradiated with the light. The image captured by the image capturing unit of the visual line sensor 142 is output to the processor unit 200.

The iris sensor 144 detects the iris of the eyeball of the user who wears the HMD 100. For example, the iris sensor 144 includes an image sensor such as CMOS or CCD and an arithmetic processing unit that acquires an iris image from the image of the captured eyeball, performs polar coordinate transformation and feature extraction, and calculates iris authentication information for performing iris authentication. The iris authentication information acquired by the iris sensor 144 is used for acquiring user identification information indicating a user attribute of the user who wears the HMD 100. The iris sensor 144 may automatically operate, when it is detected that the user has worn the HMD 100, for example.

The gesture sensor 146 detects a gesture performed by the user who wears the HMD 100. The gesture sensor 146 is provided on the main body unit of the HMD 100, so as to detect the outside world, for example. The gesture sensor 146 is a 3D motion sensor or the like. The gesture sensor 146 acquires three-dimensional information indicating a position of an object which is detected using the sensor as a reference, and outputs the three-dimensional information to the processor unit 200.

[2.2. Processor Unit]

The processor unit 200 is a control device configured to control a device connected to the processor unit 200. Connected to the processor unit 200 are, one or a plurality of HMD's 100 among the respective HMD's 100 worn by the users P1 to P3 shown in FIG. 1, an external device such as an endoscope device, a display used for an unspecified user to view information, and the like. For example, the processor unit 200 processes the information input from the external device into information displayable on the display unit of the HMD 100 or on a display, and outputs the information to each display device. Further, the processor unit 200 switches information to be displayed on the display unit of the HMD 100 on the basis of operation input from the remote controller, the visual line detection function, and the gesture detection function of each HMD 100.

Next, a display processing function of the processor unit 200 will be described. As shown in FIG. 2, the processor unit 200 includes an image input unit 211, a detection information input unit 212, a detection information processing unit 213, an image processing unit 214, a display control unit 215, an output unit 216, an operation input unit 217, and a setting storage unit 218.

The image input unit 211 is an interface that receives an image input to the processor unit 200 from the external device. In the example shown in FIG. 2, an endoscope device 10 is shown as the external device, and at this time, to the image input unit 211, an image in which an affected area is captured by the camera (not shown) of the endoscope device 10 is input. The image input unit 211 outputs the input image to the image processing unit 214. Note that, as a medical image such as the image in which an affected area is captured acquired by the endoscope device 10, a microscope image acquired by a microscope, an ultrasonic image acquired by an ultrasonic inspection device, and the like may be input to the image input unit 211. Each of those medical images may be used as the identical image shared between a plurality of users each wearing the HMD 100. Further, vital signs information such as a blood pressure, a body temperature, a pulse frequency, and a respiration rate may also be input to the image input unit 211 from a vital signs monitor.

The detection information input unit 212 is an interface to which detection information is input from the sensor unit 140 of the HMD 100 which is connected to the processor unit 200. The detection information input to the detection information input unit 212 is output to the detection information processing unit 213.

The detection information processing unit 213 performs arithmetic processing for acquiring user identification information on the basis of the detection information input from the HMD 100 which is connected to the processor unit 200. First, the detection information processing unit 213 performs iris authentication processing on the basis of the iris authentication information acquired by the iris sensor 144. In the iris authentication processing, the detection information processing unit 213 compares iris master information of each user that has been stored in advance with the iris authentication information, and specifies a user. When authenticated, the user identification information can be acquired as information indicating a user attribute on the basis of information unique to the user (for example, a user ID) associated with the iris master information. Note that an iris master DB which stores iris master information of each user may be held inside the processor unit 200, or may be on a server which can be connected via a network. Further, the user identification information of each user may be stored in the setting storage unit 218, or may be on a server which can be connected via a network. The detection information processing unit 213 outputs the specified user ID or the user identification information of each user acquired using the user ID to the image processing unit 214.

The image processing unit 214 processes an image input to the processor unit 200 into an image to be displayed on the HMD 100. The image processing unit 214 generates a left-eye image to be displayed on the first display unit of the HMD 100 and a right-eye image to be displayed on the second display unit from, for example, an image captured by the camera of the endoscope device 10. The image on which image processing has been performed by the image processing unit 214 is output to the display control unit 215. Further, the image processing unit 214 acquires display style information of a pointer on the basis of the user identification information and generates a pointer image for each user, and outputs the pointer image to the display control unit 215.

The display control unit 215 controls information to be displayed by the display units of the HMD 100. The display control unit 215 performs control in a manner that, on the basis of an instruction to switch displays from the remote controller 102 or the detection information of the sensor unit 140, specified information is displayed. For example, the display control unit 215 determines which image among the displayable information, such as an image of the endoscope device 10 or a video see-through image, is to be displayed on the basis of the instruction to switch displays. When the display control unit 215 determines the information to be displayed by each HMD 100 and the display settings, the display control unit 215 outputs the information to each HMD 100 via the output unit 216.

The operation input unit 217 is an input unit that receives an operation input from a wearer of the HMD 100. In the present embodiment, information to be displayed on the display units of the HMD 100 can be switched by the remote controller 102, for example. An operation input to the remote controller 102 is output to the operation input unit 217 and the operation input unit 217 outputs the operation input information to the display control unit 215. The display control unit 215 outputs specified information to the HMD 100 via the output unit 216 on the basis of the instruction to switch displays from the remote controller 102.

The setting storage unit 218 is a storage unit that stores display setting information of the HMD 100 corresponding to each of the pieces of user identification information. The display setting information stored in the setting storage unit 218 includes various types of setting information such as an image quality, a direction of the image, and a placement of the image. For example, the setting information of the image quality is information indicating a set value of the brightness or the coloration of the image. The information of the direction of the image is information indicating the display direction of the image displayed on the display units. Here, the display direction of the image shows a change with respect to the display state of the image which is used as a reference.

Further, the setting storage unit 218 stores the user identification information of each user. The user identification information is information in which a user ID is associated with information such as a belonging, a type of occupation, and a class of the user are associated. Further, the user identification information includes authority information showing whether a pointer of another user is operable. The authority information is set in accordance with the user's type of occupation, class, role, and the like. Moreover, the setting storage unit 218 stores, as a pointer attribute, display style information of the pointer, such as a color, a shape, or a name displayed together with the pointer, which is associated with at least one piece of information included in the user identification information. In this manner, the image processing unit 214 can refer to the display style information of the pointer and generate a pointer image of each user.

Heretofore, the configuration of the information processing system 1 according to the present embodiment has been described.

<3. Display Control Processing>

Hereinafter, with reference to FIGS. 3 to 7, display control processing on a pointer performed in the information processing system 1 according to the present embodiment shown in FIG. 2 will be described.

[3.1. Pointer Display Processing]

Figure 3:
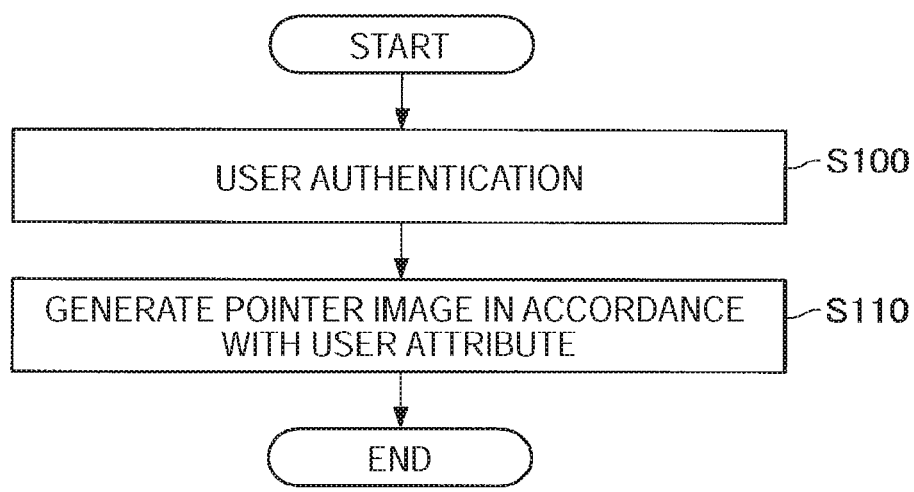
FIG. 3 is a flowchart showing pointer display processing according to the embodiment.
Figure 4:
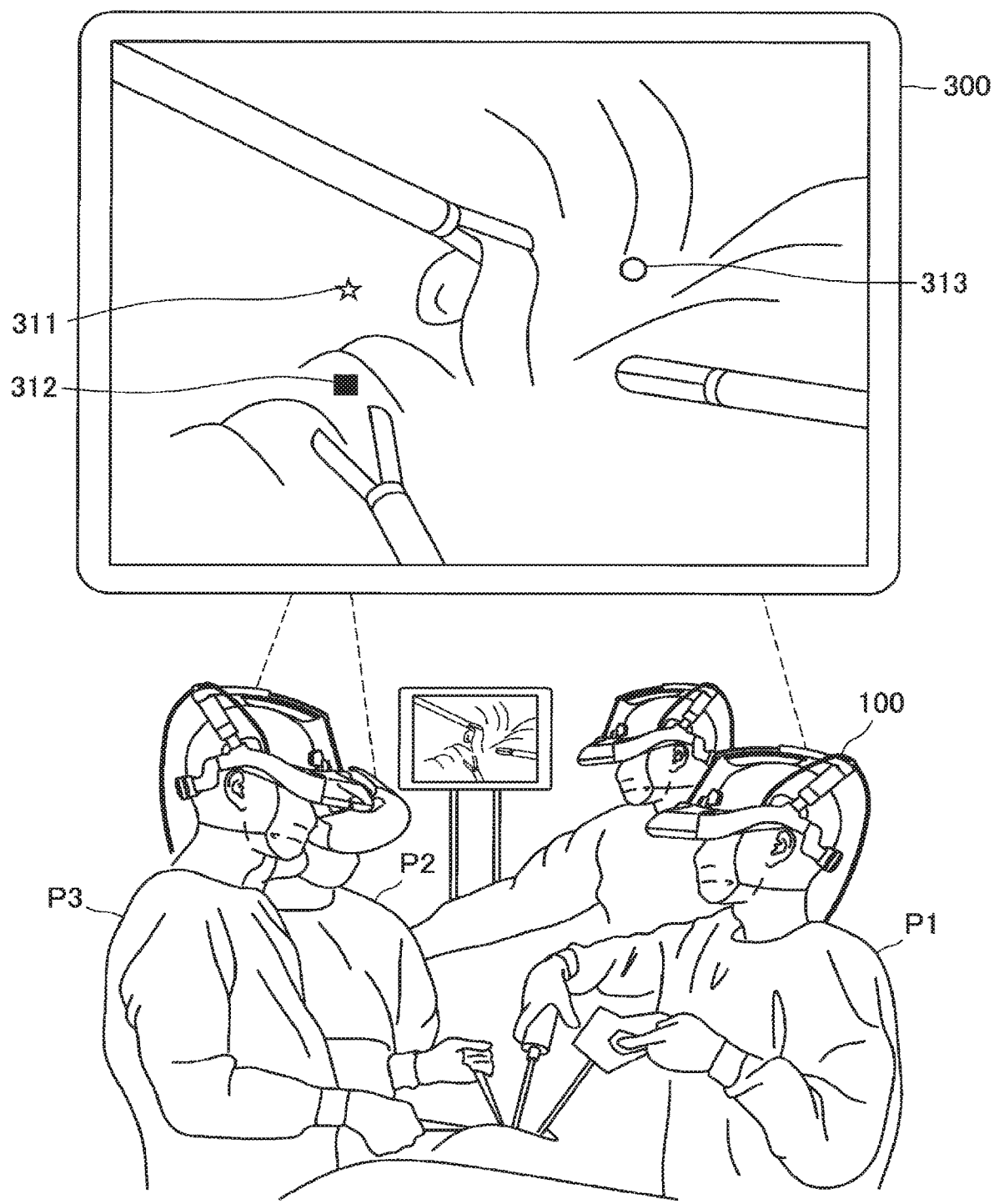
FIG. 4 is an explanatory diagram showing another example of a display style of a pointer.
Figure 5:
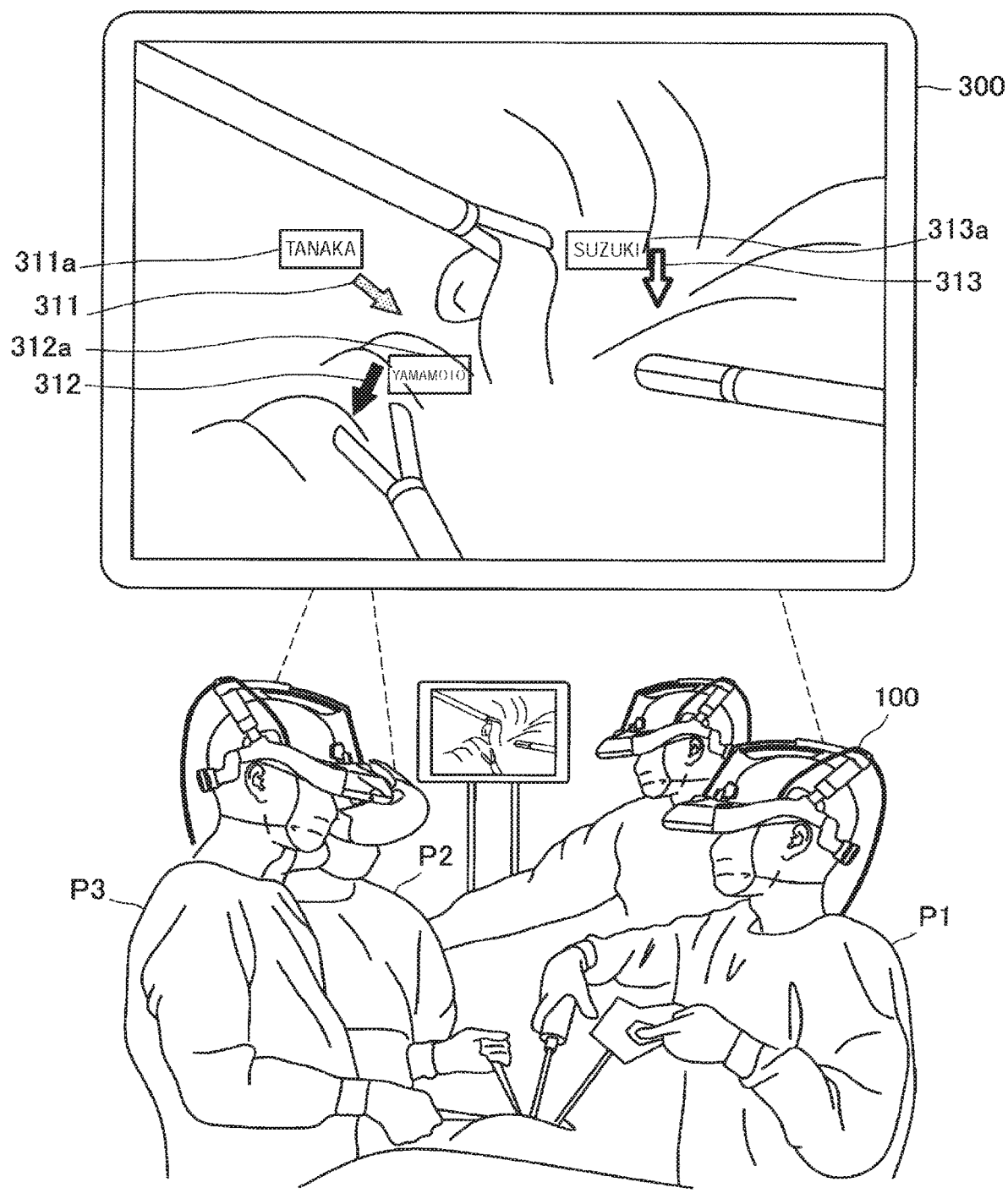
FIG. 5 is an explanatory diagram showing an example in which additional information is displayed near a pointer.

First, with reference to FIGS. 3 to 5, pointer display processing performed in the information processing system 1 according to the present embodiment will be described. FIG. 3 is a flowchart showing pointer display processing according to the embodiment. FIG. 4 is an explanatory diagram showing another example of a display style of a pointer. FIG. 5 is an explanatory diagram showing an example in which additional information is displayed near a pointer.

In the information processing system 1 according to the present embodiment, first, when a user wears the HMD 100, user authentication is performed (S100). The user authentication is performed in the detection information processing unit 213 of the processor unit 200 using iris authentication information acquired on the basis of a result detected by the iris sensor 144 of the HMD 100. The detection information processing unit 213 compares iris master information of each user that has been stored in advance with the iris authentication information, specifies a user, and acquires a user ID of the specified user.

Next, when the user is specified, the image processing unit 214 generates a pointer image of the user on the basis of user identification information indicating a user attribute (S110). The image processing unit 214 refers to the setting storage unit 218, acquires display style information of a pointer of the input user ID, and generates a pointer image of the user.

The display style information of the pointer defines a color, a shape, a user name to be displayed, and the like, and the image processing unit 214 specifies display style information of the pointer corresponding to the user attribute of the specified user, and generates the pointer image. The user identification information that determines the display style information of the pointer is set in advance, and, for example, the display style information of the pointer may be determined on the basis of authority information included in the user identification information. In the case where, for example, the authority information is classified into three levels of high, medium, and low, the pointer image of the user having a high authority is created on the basis of the display style information of the pointer set for the one having the high authority. Note that, since there are a case where the display style information of the pointer does not have the authority information and a case where there is no hierarchical relationship between the users, the display style information of the pointer may be determined not only on the basis of the authority information, but also on the basis of one or a plurality of pieces of user identification information. If a plurality of pieces of user identification information are used, it may be set such that pointer images which are the same as each other are not displayed.

The pointer image generated in Step S110 is output to the HMD 100, together with an image to be displayed on the display unit of the HMD 100. The image generation unit 120 of the HMD 100 performs predetermined processing on the input image, also calculates a display position of the pointer image from a result detected by the sensor unit 140, superimposes a pointer image signal on an image signal, and outputs the resultant to the display elements 132 and 134. An initial display position of the pointer image may be set in advance at the center of the display region, for example, or may also be a position designated by the user at this time using a visual line direction, a gesture, or the like. In this manner, the image is displayed on the display unit of the HMD 100, together with the pointer having a shape corresponding to the user attribute of the user.

In the display style information of the pointer, the users may be distinguished from each other by, as shown in FIG. 1, setting a plurality of colors and using an identical shape (arrow), or by, as shown in FIG. 4, setting shapes of the pointer (star-shape, circle, square, and the like). Further, additional information of the pointer that specifically indicates the user may also be set in the display style information of the pointer. For example, as shown in FIG. 5, pieces of pointer additional information 311*a*, 312*a*, and 313*a*, which display user names, respectively, are displayed near the respective pointers, and thus make it possible to distinguish the users more clearly. Note that, although the user names are displayed as the pieces of pointer additional information in FIG. 5, the roles in the surgery, such as a surgeon, an assistant, and the like, may be displayed as the pieces of pointer additional information.

Owing to the pointer display processing, a pointer is displayed on the display unit of the HMD 100, in this case, however, in the case where a plurality of users are observing the image displayed on the display unit, the pointer(s) of the other user(s) is(/are) also displayed on the display unit. That is, in the case where the image being observed is a shared image which is shared between the plurality of users, a plurality of pointers are displayed, and as described above, the respective pointers of the users are displayed differently in accordance with the respective user attributes. Accordingly, also in the case where an image is shared between the plurality of users, the pointers corresponding to the respective users can be grasped clearly, and the users can communicate with each other smoothly.

[3.2. Pointer Operation Processing]

Figure 6:
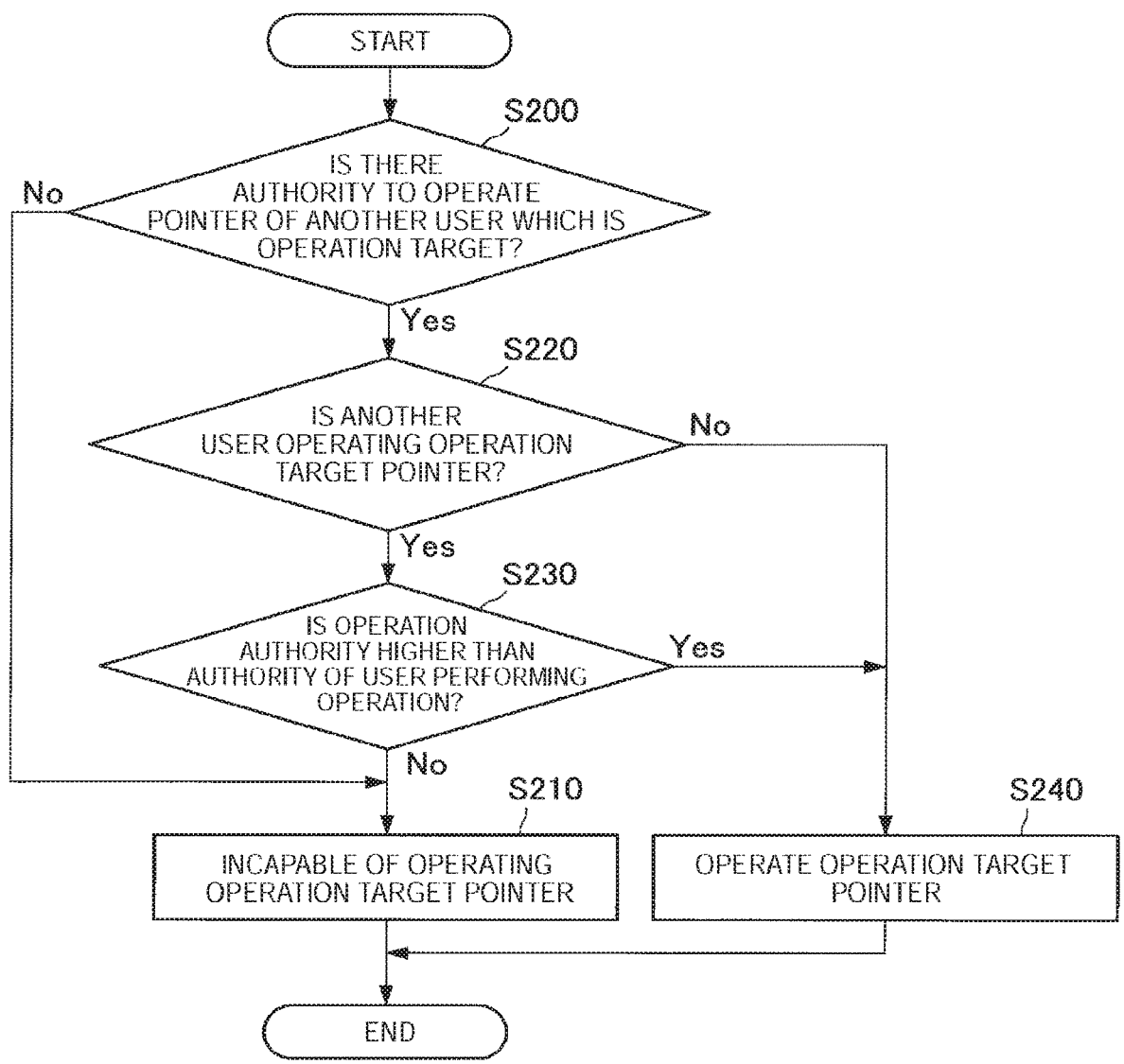
FIG. 6 is a flowchart showing pointer operation processing according to the embodiment.
Figure 7:
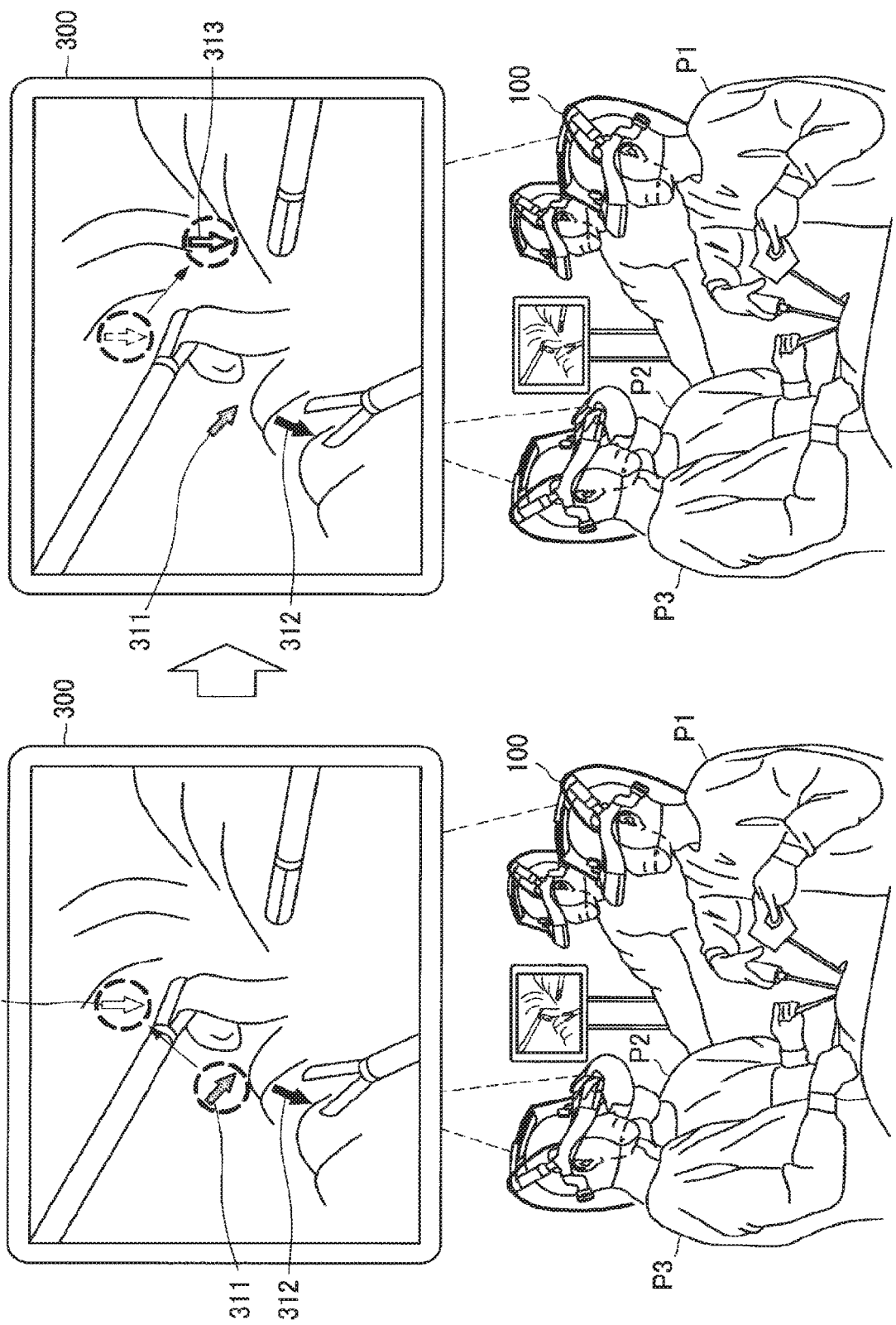
FIG. 7 is an explanatory diagram illustrating pointer operation processing according to the embodiment.

In the present embodiment, in the case where an image is shared between a plurality of users, a pointer of another user may be operable on the basis of pieces of authority information of the users. Hereinafter, with reference to FIGS. 6 and 7, pointer operation processing performed in the information processing system 1 according to the present embodiment will be described. Note that FIG. 6 is a flowchart showing pointer operation processing according to the embodiment. FIG. 7 is an explanatory diagram illustrating pointer operation processing according to the embodiment.

The pointer operation processing according to the present embodiment is processing involving determining, by the detection information processing unit 213, for example, whether a pointer of another user is operable on the basis of the pieces of authority information of the users. This processing is performed, for example, in the case where an image is shared between a plurality of users and a plurality of pointers are displayed on the display unit, a user issues an instruction to change a pointer that the user operates. The instruction to change a pointer which is an operation target may be issued by a foot switch or a gesture. Hereinafter, description will be made using a situation in which, as shown in FIG. 7, users P1 to P3 share an image 300. In FIG. 7, the pointers of the users P1, P2, and P3 correspond to a pointer 311, a pointer 312, and a pointer 313, respectively. Let us assume the case where the user P1 operates the pointer 313 of the user P3.

In such a situation, first, the detection information processing unit 213 determines whether the pointer 313 of the user P3 is operable by the user P1 (S200). Whether the user P1 has an intention to operate the pointer 313 of the user P3 may be determined on the basis of whether a position designated by the user P1 is at the display position of the pointer 313 of the user P3, for example. The position designated by the user P1 is specified by a result detected by the visual line sensor 142 or the gesture sensor 146. Let us assume that the detection information processing unit 213 detects, on the basis of the result detected by the visual line sensor 142 or the gesture sensor 146 of the HMD 100 worn by the user P1, that the position designated by the user P1 is at the display position of the pointer 313 of the user P3, and that the user P1 designates the pointer 313 of the user P3. Then, the detection information processing unit 213 confirms the authority information of the user P1 and the authority information of the user P3. The authority information is acquired from the user identification information stored in the setting storage unit 218. The detection information processing unit 213 compares the authority information of the user P1 with the authority information of the user P3, and specifies a user having a higher authority. In the case where the user P1 has an authority higher than the authority of the user P3, the user P1 has the authority to operate the pointer 313 of the user P3, and the processing proceeds to Step S220.

On the other hand, in the case where the user P1 has an authority that is the same as or lower than the authority of the user P3, the user P1 does not have the authority to operate the pointer 313 of the user P3. In this case, the operation of the pointer 313 which is an operation target cannot be performed (S210), and the processing is finished. At this time, the detection information processing unit 213 generates information showing that the pointer 313 of the user P3 cannot be operated, outputs the information to the HMD 100 via the output unit 216, and thus may notify the user P1 of the information through a message or an audio.

Next, in the case where the user P1 has the authority to operate the pointer 313 of the user P3, the detection information processing unit 213 determines whether a user other than the user P1 is operating the pointer 313 (S220). There may be a case where a user other than the user P3, who is the original user of the pointer 313, is operating the pointer 313. Accordingly, if the user P3 is operating the pointer 313, the detection information processing unit 213 determines whether the user P1 has the authority higher than the authority of the user who is operating the pointer 313 (S230).

In the case where the user P1 has the authority higher than the authority of the user who is operating the pointer 313, the detection information processing unit 213 determines that the user P1 can operate the pointer 313 instead of the other user who is performing the operation (S240). On the other hand, in Step S230, in the case where the authority of the user P1 is the same as or lower than the authority of the user who is operating the pointer 313, the detection information processing unit 213 determines that the user P1 cannot operate the pointer 313, which is an operation target (S210), and the processing is finished.

Note that, in the case where it is determined in Step S220 that the pointer 313 is not being operated, the user P1 can operate the pointer 313 (S240).

Whether the pointer of the other user is operable is determined through the above processing, and the operability information is output to the HMD 100 via the output unit 216 together with the image generated by the display control unit 215 and the pointer image. The image generation unit 120 of the HMD 100 generates, on the basis of those pieces of information, image signals to be output to the display elements 132 and 134, respectively, and pointer image signals of the respective users who are observing the shared image.

Here, in the case where the instruction to change a pointer to be an operation target is issued, image generation unit 120 confirms whether the display position of the pointer of the other user is changeable on the basis of the result determined in the processing of FIG. 6. In the case where the display position of the pointer of the other user is changeable, the image generation unit 120 changes the display position of the pointer of the other user on the basis of a visual line position or a gesture of the user himself/herself. In this case, the pointer of the user himself/herself is not moved. The image generation unit 120 superimposes a pointer image signal on an image signal which has been generated on the basis of the information from the processor unit 200, and outputs the resultant to the display elements 132 and 134. The operation of the pointer of the other user which has become operable is continued until the instruction to change the pointer which is an operation target to the original pointer, or the instruction to change the pointer to be an operation target to a pointer of still another user is issued from the user.

Heretofore, the pointer operation processing according to the present embodiment has been described. In this manner, a pointer of another user is made operable on the basis of the pieces of authority information of the users, and thus, a user having a high authority can operate a pointer of a user having a low authority, and can give instructions of work directly to the user having the low authority.

Regarding a hierarchical relationship of authorities, in the case of a surgery such as an endoscopic surgery, a surgeon has a high authority and an assistant has a low authority. In the case of a medical diagnosis such as an ultrasonic diagnosis, the levels of authority decreases in the following order: a doctor, a clinical examination technician, and then a patient. In the case of telemedicine, a medical worker who gives instructions to a distant patient has a high authority, and the distant patient has a low authority. Further, in the educational interface, an educator has a high authority, and a student has a low authority.

Further, in the above example, the case where whether a pointer of another user is operable is determined in accordance with pieces of authority information has been described, but the present disclosure is not limited to such an example, and, for example, the number of pointers to be displayed on the display unit of the HMD 100 of each user may be changed in accordance with the authority information. For example, in an endoscopic surgery, it is assumed that a surgeon, an assistant, and a scopist who operates an endoscope device each wear the HMD 100, and there is a situation in which all the users share and observe an identical image during the surgery.

Here, the levels of authority decreases in the following order: the surgeon, the assistant, and the scopist, however, there are many cases in which the surgeon and the assistant, who have higher authorities than the scopist, do not necessarily have the pointer of the scopist displayed. In this case, on the basis of the pieces of authority information of the surgeon, the assistant, and the scopist, the pointer(s) of the other user(s) whose authority(/authorities) is(/are) lower than the authority of the user himself/herself may be hidden. In this manner, only information which is more necessary can be displayed on the display unit, and the user can more easily recognize the information displayed on the display unit. Therefore, mutual communication in carrying out a surgery while sharing an image between a plurality of persons becomes smooth, and the surgery can be conducted smoothly.

CONCLUSION

Heretofore, the information processing system 1 including the HMD 100 according to the present embodiment has been described. According to the present embodiment, when a plurality of users each wearing the HMD 100 share and observe an image, the pointers operated by the respective users are displayed on a display region by changing display styles of the pointers on the basis of user attributes of the respective users. In this manner, even in the case where a plurality of pointers are displayed on the display region, the pointers are displayed in different colors or shapes, and hence, a user can recognize clearly the pointer that the user can operate, and also can recognize clearly which users operate which other pointers.

Further, the information processing system 1 according to the present embodiment may make a pointer of another user operable in accordance with pieces of authority information included in user attributes. In this manner, a user having a high authority can operate a pointer of a user having a low authority, and can give instructions of work directly to the user having the low authority.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the above embodiment, the user identification information which is a user attribute is acquired on the basis of the iris authentication information acquired by the iris sensor, but the present disclosure is not limited to such an example. For example, the user identification information may be acquired on the basis of biometric authentication information other than the iris authentication information, or may be acquired from an IC card or the like having user identification information stored therein using near field communication (NFC).

Figure 8:
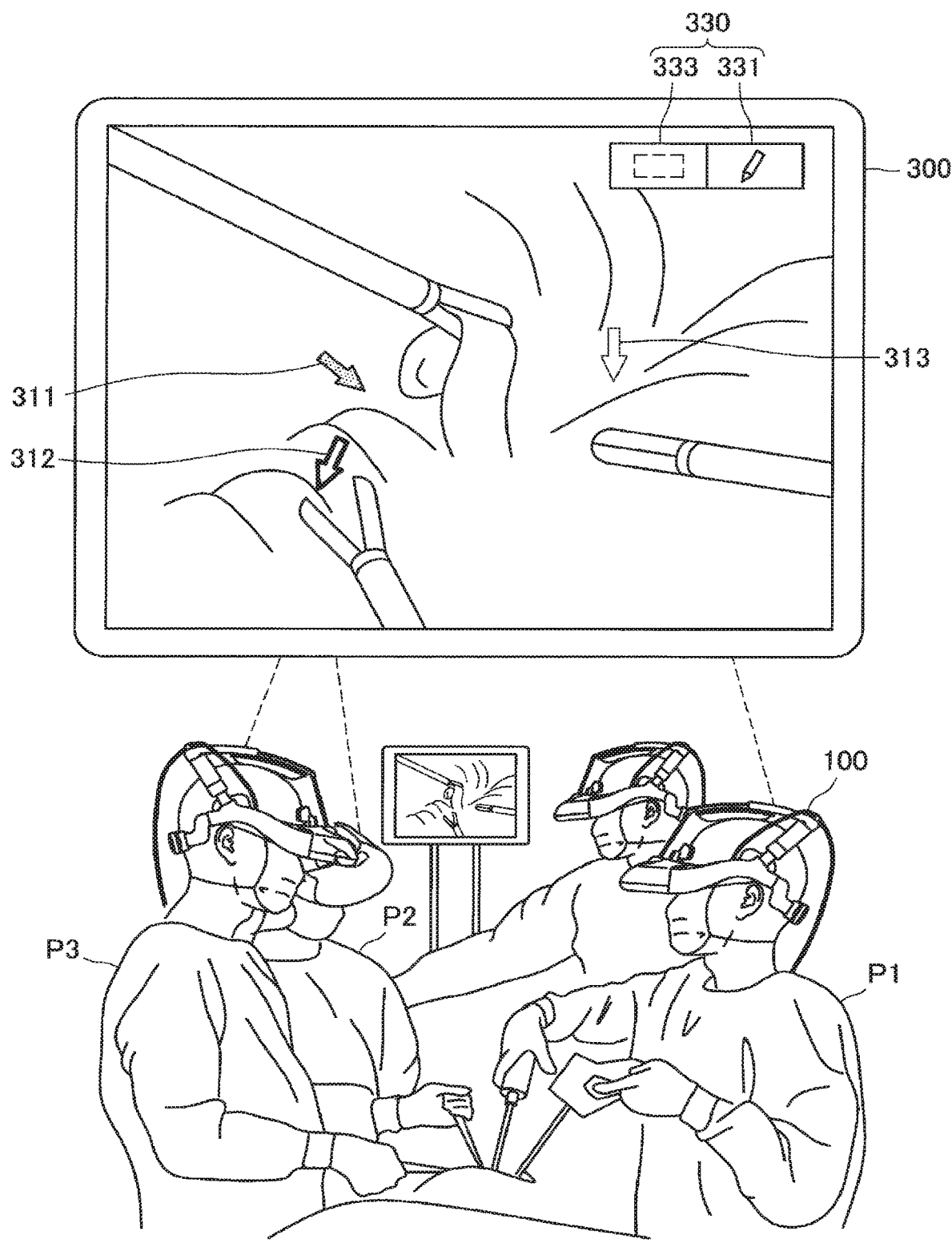
FIG. 8 is an explanatory diagram showing a display example of an HMD in the case where a paint function is provided.

Further, in the embodiment described above, the information processing system capable of indicating a specified part by displaying a pointer on the display region of the HMD has been described, but the present disclosure is not limited to such an example. For example, as shown in FIG. 8, a paint function may further be included, which causes a line or a figure to be displayed in a superimposed manner on the display region. In FIG. 8, at the upper right of the display region, there are, as paint objects 330, a pen icon 331 which enables drawing of a line and a figure icon 333 which enables entering of a figure. Using those, the user can select an icon using the visual line, and can draw a line using the visual line at a desired part by moving the visual line, for example. Further, such operations can be performed by a gesture, in addition to the visual line.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:
a processing unit configured to change a pointer attribute of a pointer displayed in accordance with a position designated by a user on a display region of a head mounted display, on the basis of a user attribute of the user who wears the head mounted display.

(2)

The information processing apparatus according to (1), in which
the processing unit displays, on each of display regions of head mounted displays that a plurality of users wear, respectively, an identical image shared between the users and pointers of at least one or more users out of the plurality of users.

(3)

The information processing apparatus according to (2), in which
the processing unit determines whether a pointer of another user is displayable on the basis of a relationship of user attributes between the users.

(4)

The information processing apparatus according to (2) or (3), in which
the processing unit determines whether a pointer of another user is operable on the basis of a relationship of user attributes between the users.

(5)

The information processing apparatus according to any one of (2) to (4), in which
the identical image shared between the users is a medical image.

(6)

The information processing apparatus according to any one of (1) to (5), in which
the user attribute is authority information of the user.

(7)

The information processing apparatus according to (6), in which
the authority information of the user is authority information between medical workers.

(8)

The information processing apparatus according to any one of (1) to (7), in which
the user attribute is acquired through biometric authentication.

(9)

The information processing apparatus according to any one of (1) to (8), in which
the user attribute is acquired through near field communication.

(10)

The information processing apparatus according to any one of (1) to (9), in which
the pointer attribute is display style information of the pointer.

(11)

The information processing apparatus according to (10), in which
the display style information of the pointer is information on a shape or a color of the pointer.

(12)

The information processing apparatus according to any one of (1) to (11), in which
the position designated by the user is determined by a visual line of the user.

(13)

The information processing apparatus according to any one of (1) to (11), in which
the position designated by the user is determined by a gesture of the user.

(14)

An information processing method including:
acquiring a user attribute of a user who wears a head mounted display; and
changing a pointer attribute of a pointer displayed in accordance with a position designated by the user on a display region of the head mounted display, on the basis of the user attribute.

(15)

An information processing system including:
a head mounted display; and
a processing unit configured to change a pointer attribute of a pointer displayed in accordance with a position designated by a user on a display region of the head mounted display, on the basis of a user attribute of the user who wears the head mounted display.

(16)

The information processing system according to (15), in which
the head mounted display includes a visual line sensor.

(17)

The information processing system according to (15) or (16), in which
the head mounted display includes a gesture sensor.

(18)

The information processing system according to any one of (15) to (17), further including:
an image capturing device configured to capture an image of an affected area.

REFERENCE SIGNS LIST 1 information processing system
10 endoscope device
100 HMD
102 remote controller
110 display port
120 image generation unit
132 first display element
134 second display element
140 sensor unit
142 visual line sensor
144 iris sensor
146 gesture sensor
200 processor unit
211 image input unit
212 detection information input unit
213 detection information processing unit
214 image processing unit
215 display control unit
216 output unit
217 operation input unit
218 setting storage unit

The invention claimed is:

1. An information processing apparatus comprising:
processing circuitry configured to
control display, on plural head mounted displays, respectively, of an identical image acquired from a perspective and shared between the plural head mounted displays,
display a plurality of a pointer icons on the identical image, wherein each of the plurality of pointer icons is associated with a respective one of a plurality of users wearing a respective one of the plural head mounted displays, and a position of each of the plurality of pointer icons on the identical image is determined by a visual line of the respective one of the plurality of users, and
change a display attribute of a first pointer icon of the plurality of pointer icons based on a user attribute of a respective first user of the plurality of users, wherein the user attribute is authority information of the first user.

2. The information processing apparatus according to claim 1, wherein
the processing circuitry determines whether a first pointer icon associated with a first user is displayable on a head mounted display of a second user on the basis of a relationship between user attributes of the first user and the second user.

3. The information processing apparatus according to claim 1, wherein
the processing circuitry determines whether a first pointer icon of a first user is operable on the basis of a relationship between user attributes of the first user and a second user.

4. The information apparatus according to claim 1, wherein
the identical image acquired from the perspective and shared between the plural head mounted displays is a medical image.

5. The information processing apparatus according to claim 1, wherein
the authority information of the first user is authority information between medical workers.

6. The information processing apparatus according to claim 1, wherein
the user attribute is acquired through biometric authentication.

7. The information processing apparatus according to claim 1, wherein
the user attribute is acquired through near field communication.

8. The information processing apparatus according to claim 1, wherein
the display attribute comprises display style information of the pointer.

9. The information processing apparatus according to claim 8, wherein
the display style information of the pointer is information on a shape or a color of the pointer.

10. The information processing apparatus according to claim 1, wherein
the position of a first pointer icon of the plurality of icons is further determined by a gesture of a first user of the plurality of users.

11. The information processing apparatus according to claim 1, wherein the processing circuitry is further configured to display each of the plurality of pointer icons with at least one of a different shape and a different color.

12. The information processing apparatus according to claim 11, wherein the processing circuitry is further configured to display each of the plurality of pointer icons with an ID and a class of the respective user.

13. The information processing apparatus according to claim 1, wherein
the plurality of users comprises a first user and a second user, and
when the first user has a higher authority than the second user, the first user is able to operate the pointer icon associated with the second user.

14. An information processing method comprising:
controlling display, on plural displays located in front of a left eye and a right eye of a respective user, of an identical image acquired from a perspective and shared between the plural displays;
displaying a plurality of pointer icons on the identical image;
acquiring a user attribute associated with a display of the plural displays; and
changing, on the basis of the user attribute, a pointer attribute of a first pointer icon of the plurality of pointer icons displayed in a designated position on the identical image displayed on the plural displays, wherein each of the plurality of pointer icons is associated with a respective one of the plural displays, and a position of each of the plurality of pointer icons on the identical image is determined by a visual line of the respective user of the respective one of the plural displays,
wherein the user attribute is authority information of the user.

15. An information processing system comprising:
a display; and
processing circuitry configured to
control display, on the display, of an identical image acquired from a perspective and shared between plural displays, and
display a plurality of pointer icons on the identical image, wherein each of the plurality of pointer icons is associated with a respective one of a plurality of users wearing a respective one of the plural displays, and a position of each of the plurality of pointer icons on the identical image is determined by a visual line of the respective one of the plurality of users, and
change a display attribute of a first pointer icon of the plurality of pointer icons based on a user attribute of a respective first user of the plurality of users, wherein the user attribute is authority information of the first user.

16. The information processing system according to claim 15, wherein
the display includes a visual line sensor.

17. The information processing system according to claim 15, wherein
the display includes a gesture sensor.

18. The information processing system according to claim 15, further comprising
an image capturing device configured to capture an image of an affected area from the perspective.

* * * * *